United States Patent [19]

Schmetzer et al.

[11] Patent Number: 4,468,397
[45] Date of Patent: Aug. 28, 1984

[54] COMBATING PESTS WITH NOVEL IMINO ETHERS

[75] Inventors: Johannes Schmetzer, Cologne; Jörg Stetter, Wuppertal; Ingeborg Hammann, Cologne; Bernhard Homeyer, Leverkusen, all of Fed. Rep. of Germany

[73] Assignee: Bayer Aktiengesellschaft, Leverkusen, Fed. Rep. of Germany

[21] Appl. No.: 307,337

[22] Filed: Sep. 30, 1981

[30] Foreign Application Priority Data

Oct. 17, 1980 [DE] Fed. Rep. of Germany ....... 3039269

[51] Int. Cl.³ .................... A01N 43/08; A01N 43/10; A01N 43/18; A01N 43/20
[52] U.S. Cl. .......................... 424/248.51; 260/453.3; 260/453.8; 424/298; 424/275; 549/424; 549/480; 549/510; 549/511; 549/28; 549/68; 549/88
[58] Field of Search .......................... 260/453.3, 453.8; 424/298, 248.51, 275; 549/424, 480, 510, 511, 28, 68, 88

[56] References Cited

FOREIGN PATENT DOCUMENTS 2111459 3/1971 Fed. Rep. of Germany ... 260/453.3
7714199 5/1977 France .............................. 260/453.3

*Primary Examiner*—Henry R. Jiles
*Assistant Examiner*—Robert C. Whittenbaugh
*Attorney, Agent, or Firm*—Sprung Horn Kramer & Woods

[57] ABSTRACT

Hydroxamic acid esters of the formula

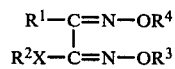
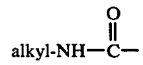

in which
$R^1$ is an optionally substituted alkyl, cycloalkyl, aryl or aralkyl radical and
$R^2$ is an alkyl, alkenyl or alkinyl radical, or
$R^1$ and $R^2$ together are an alkylene bridge with 2 to 4 carbon atoms,
one of the radicals $R^3$ and $R^4$ is $$\text{alkyl-NH}-\overset{\overset{\displaystyle O}{\|}}{C}-$$

while the other is an alkyl, alkenyl, alkinyl, halogenoalkenyl or alkoxyalkyl radical, and
X is O or S, which possess pesticidal properties. Intermediates therefor wherein one of $N-OR^3$ and $N-OR^4$ is $N-OH$ or a carbonyl group are also new.

11 Claims, No Drawings

COMBATING PESTS WITH NOVEL IMINO ETHERS

The present invention relates to certain new hydroxamic acid esters, to a process for their production, to their use in agents for combating pests, and to novel intermediate products for their preparation and to processes for the production of these intermediate products.

It has already been disclosed that methylthiosubstituted oxime-carbamates, such as 3,3-dimethyl-2-methylcarbamoyloximino-1-methylthio-butane (see German Offenlegungsschrift (German Published Specification) No. 2,216,838) have insecticidal and acaricidal properties. However, these compounds are not completely satisfactory, especially when low concentrations are applied.

The present invention now provides, as new compounds, the hydroxamic acid esters of the general formula

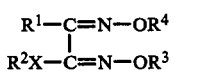  (I)

in which
$R^1$ represents an optionally substituted alkyl, cycloalkyl, aryl or aralkyl radical and
$R^2$ represents an alkyl, alkenyl or alkinyl radical, or
$R^1$ and $R^2$ together represent an alkylene bridge with 2 to 4 carbon atoms,
one of the radicals $R^3$ or $R^4$ represents a radical of the general formula

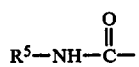

in which
$R^5$ represents an alkyl radical,
whilst the other radical $R^3$ or $R^4$ represents an alkyl, alkenyl, alkinyl, halogenoalkyl, halogenoalkenyl or alkoxyalkyl radical, and
X represents O or S.

According to the present invention there is further provided a process for the production of a compound of formula (I) of the present invention, characterized in that an oxime of the general formula

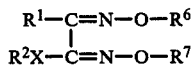  (II)

in which
$R^1$, $R^2$ and X have the abovementioned meanings and one of the radicals $R^6$ or $R^7$ represents a hydrogen atom and the other radical $R^6$ and $R^7$ represents an alkyl, alkenyl, alkinyl, halogenoalkyl, halogenoalkenyl or alkoxyalkyl radical,
is reacted with an isocyanate of the general formula

  (III)

in which $R^5$ has the abovementioned meaning.

The present invention further provides, as new compounds, the intermediate compounds of formula (II), as defined above.

According to the present invention, there is further provided a process for the production of a novel intermediate of formula (II) characterized in that a ketone of the general formula

  (IV)

in which
$R^1$, $R^2$ and X have the abovementioned meanings and
$R^8$ represents a hydrogen atom or a radical given in the definition of $R^7$,
(a) in the case where $R^8$ represents hydrogen, is reacted with a hydroxylamine ether, or a salt thereof, of the general formula $R^6ONH_2 xHY$  (V)

in which
$R^6$ has the abovementioned meaning and
Y represents an anion of an acid, or
(b) in the case where $R^8$ represents the radicals given in the definition of $R^7$, is reacted with hydroxylamine or a salt thereof.

The present invention further provides, as new compounds, the intermediate compounds of formula (IV), as defined above.

According to the present invention there is further provided a process for the production of a novel intermediate of formula (IV) characterized in that
(α) in the case where $R^8$ represents a hydrogen atom, a ketone of the general formula

  (VI)

in which
$R^1$, $R^2$ and X have the abovementioned meanings, is reacted with a nitrosating agent and
(β) in the case where $R^8$ represents a radical given in the definition of $R^7$, a compound obtained in process variant (α), of the general formula

  (VII)

in which $R^1$, $R^2$ and X have the abovementioned meanings, is reacted with a compound of the general formula

  (VIII)

in which
$R^7$ has the abovementioned meaning and
W represents Cl, Br or $R^7OSO_2O$.

The compounds of the formula (I) can be in the syn-form or anti-form; they are predominantly obtained as a mixture of the two forms.

The compounds of the formula (I) are suitable for combating pests; in particular, they have powerful insecticidal, acaricidal and nematicidal properties.

Surprisingly, the compounds of the formula (I) exhibit a more powerful insecticidal and acaricidal action than the known compound 3,3-dimethyl-2-methylcarbamoyloximino-1-methylthio-butane.

Preferred hydroxamic acid esters of the formula (I) according to the invention are those in which $R^1$ represents an alkyl radical with 1 to 4 carbon atoms, a halogenoalkyl radical with 1 to 4 carbon atoms and up to 5 halogen atoms (such as preferably, fluorine, chlorine or bromine atoms), a cycloalkyl radical with up to 8 carbon atoms, an alkoxyalkyl or alkylthioalkyl radical with up to 3 carbon atoms in each alkyl part, or an optionally substituted phenyl radical (preferred substituents which may be mentioned being: halogen—in particular fluorine, chlorine and bromine—and cyano, nitro and alkyl with 1 or 2 carbon atoms), $R^2$ represents an alkyl radical with 1 to 4 carbon atoms, an alkenyl radical with 1 to 4 carbon atoms or an alkinyl radical with 1 to 4 carbon atoms, or $R^1$ and $R^2$ together represent an optionally methyl-substituted methylene, ethylene or propylene bridge, one of the radicals $R^3$ or $R^4$ represents an alkyl radical with 1 to 4 carbon atoms, an alkenyl radical with 2 to 4 carbon atoms, an alkinyl radical with 2 to 4 carbon atoms, a halogenoalkyl radical with 1 to 4 carbon atoms and up to 3 halogen atoms, a halogenoalkenyl radical with 2 to 4 carbon atoms and up to 3 halogen atoms or an alkoxyalkyl radical with up to 2 carbon atoms in each alkyl part, and the other radical $R^3$ or $R^4$ represents the radical

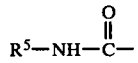

in which $R^5$ represents a methyl or ethyl radical, and X represents S.

Very particularly preferred hydroxamic acid esters of the formula (I) are those in which $R^1$ represents a methyl, ethyl, propyl, isopropyl, tert.-butyl or fluoro-, chloro-, bromo-, difluoro- or dichloro-tert.-butyl radical; and $R^2$ represents a methyl or ethyl radical; or $R^1$ and $R^2$ together represent an ethylene bridge; one of the radicals $R^3$ or $R^4$ represents a methyl, ethyl, propargyl or allyl radical and the other radical $R^3$ or $R^4$ represents a methylcarbamoyl radical; and X represents S.

The following compounds may be mentioned specifically, in addition to the preparative examples and the examples in the tables:

$$R^1-C=N-O-R^4$$
$$R^2X-C=N-O-R^3 \quad (I)$$

| $R^1$ | $R^2$ | $R^3$ | $R^4$ | X |
|---|---|---|---|---|
| $(CH_3)_3C-$ | $CH_3$ | $CH_3$ | $CH_3NH-CO-$ | S |
| " | " | $C_2H_5$ | " | " |
| " | " | $C_3H_7$ | " | " |
| " | " | $-CH_2-C\equiv CH$ | " | " |
| " | " | $-CH_2-CH=CH_2$ | " | " |
| " | " | $-CH_2-C(CH_3)=CH_2$ | " | " |
| " | " | $CH_3$ | " | " |
| " | " | $C_2H_5$ | " | " |
| " | " | $C_3H_7$ | " | " |
| " | $C_2H_5$ | $-CH_2-C\equiv CH$ | " | " |
| " | " | $-CH_2-CH=CH_2$ | " | " |
| " | $C_3H_7$ | $CH_3$ | " | " |
| " | " | $C_2H_5$ | " | " |
| " | $-CH_2-CH=CH_2$ | $CH_3$ | " | " |
| " | " | $C_2H_5$ | " | " |
| $R^1 + R^2$ | | | | |
| $\begin{array}{c} CH_3 \\ | \\ -C-CH_2- \\ | \\ CH_3 \end{array}$ | | $CH_3$ | " | " |
| " | | $C_2H_5$ | " | " |
| " | | $-CH_2-C\equiv CH$ | " | " |
| " | | $-CH_2-CH=CH_2$ | " | " |
| $R^1 + R^2$ | | | | |
| $-CH_2-CH_2-$ | | $CH_3$ | " | " |
| " | | $C_2H_5$ | " | " |
| " | | $-CH-C\equiv CH$ | " | " |
| " | | $-CH_2-CH=CH_2$ | " | " |
| $R^1 + R^2$ | | | | |
| $-CH_2-CH_2-CH_2-$ | | $CH_3$ | " | " |
| " | | $C_2H_5$ | " | " |
| " | | $-CH_2-C\equiv CH$ | " | " |
| " | | $-CH_2-CH=CH_2$ | " | " |
| $(CH_3)_2HC-$ | $CH_3$ | $CH_3$ | " | " |
| " | " | $C_2H_5$ | " | " |
| " | " | $C_3H_7$ | " | " |
| " | " | $-CH_2-C\equiv CH$ | " | " |
| " | " | $-CH_2-CH=CH_2$ | " | " |
| " | " | $-CH_2-C(CH_3)=CH_2$ | " | " |
| " | $C_2H_5$ | $CH_3$ | " | " |
| " | " | $C_2H_5$ | " | " |
| " | " | $C_3H_7$ | " | " |
| " | " | $-CH_2-C\equiv CH$ | " | " |
| " | " | $-CH_2-CH=CH_2$ | " | " |
| " | $C_3H_7$ | $CH_3$ | " | " |
| " | " | $C_2H_5$ | " | " |
| " | $-CH_2-CH=CH_2$ | $CH_3$ | " | " |

-continued $$R^1-C=N-O-R^4 \quad (I)$$
$$R^2X-C=N-O-R^3$$

| R¹ | R² | R³ | R⁴ | X |
|---|---|---|---|---|
| " | " | C₂H₅ | " | " |
| CH₃S-C(CH₃)₂- | CH₃ | CH₃ | " | " |
| " | " | C₂H₅ | " | " |
| " | " | C₃H₇ | " | " |
| " | CH₃ | -CH₂-C≡CH | " | " |
| " | " | -CH₂-CH=CH₂ | " | " |
| " | " | -CH₂-C(CH₃)=CH₂ | " | " |
| " | C₂H₅ | CH₃ | " | " |
| " | " | C₂H₅ | " | " |
| " | " | C₃H₇ | " | " |
| " | " | -CH₂-C≡CH | " | " |
| " | " | -CH₂-CH=CH₂ | " | " |
| " | C₃H₇ | CH₃ | " | " |
| " | " | C₂H₅ | " | " |
| " | -CH₂-CH=CH₂ | CH₃ | " | " |
| " | " | C₂H₅ | " | " |
| FCH₂-C(CH₃)₂- | CH₃ | CH₃ | " | " |
| " | " | C₂H₅ | " | " |
| " | " | C₃H₇ | " | " |
| " | " | -CH₂-C≡CH | " | " |
| " | " | -CH₂-CH=CH₂ | " | " |
| " | " | -CH₂-C(CH₃)=CH₂ | " | " |
| " | C₂H₅ | CH₃ | " | " |
| " | " | C₂H₅ | " | " |
| " | " | C₃H₇ | " | " |
| " | " | -CH₂-C≡CH | " | " |
| " | " | -CH₂-CH=CH₂ | " | " |
| " | C₃H₇ | CH₃ | " | " |
| " | " | C₂H₅ | " | " |
| " | -CH₂-CH=CH₂ | CH₃ | " | " |
| " | " | C₂H₅ | " | " |
| ClCH₂-C(CH₃)₂- | CH₃ | CH₃ | " | " |
| " | " | C₂H₅ | " | " |
| " | " | C₃H₇ | " | " |
| " | " | -CH₂-C≡CH | " | " |
| " | " | -CH-CH=CH₂ | " | " |
| " | " | -CH₂-C(CH₃)=CH₂ | " | " |
| " | C₂H₅ | CH₃ | " | " |
| " | " | C₂H₅ | " | " |
| " | " | C₃H₇ | " | " |
| " | " | -CH₂-C≡CH | " | " |
| " | " | -CH₂-CH=CH₂ | " | " |
| " | C₃H₇ | CH₃ | " | " |
| " | " | C₂H₅ | " | " |
| " | -CH₂-CH=CH₂ | CH₃ | " | " |
| " | " | C₂H₅ | " | " |
| FCH₂-C(CH₂F)(CH₃)- | CH₃ | CH₃ | " | " |
| " | " | C₂H₅ | " | " |
| " | " | C₃H₇ | " | " |
| " | " | -CH₂-C≡CH | " | " |
| " | " | -CH₂-CH=CH₂ | " | " |
| " | " | -CH₂-C(CH₃)=CH₂ | " | " |
| " | C₂H₅ | CH₃ | " | " |
| " | " | C₂H₅ | " | " |

-continued $$R^1-C=N-O-R^4 \quad (I)$$
$$R^2X-C=N-O-R^3$$

| R¹ | R² | R³ | R⁴ | X |
|---|---|---|---|---|
| " | " | C₃H₇ | " | " |
| " | " | —CH₂—C≡CH | " | " |
| " | " | —CH₂—CH=CH₂ | " | " |
| " | C₃H₇ | CH₃ | " | " |
| " | " | C₂H₅ | " | " |
| " | —CH₂—CH=CH₂CH₃ | | " | " |
| " | —CH₂—CH=CH₂C₂H₅ | | " | " |
| CH₃ | CH₃ | CH₃ | " | " |
| " | " | C₂H₅ | " | " |
| " | " | C₃H₇ | " | " |
| " | " | —CH₂—C≡CH | " | " |
| " | " | —CH₂—CH=CH₂ | " | " |
| " | " | —CH₂—C(CH₃)=CH₂ | " | " |
| " | C₂H₅ | CH₃ | " | " |
| " | " | C₂H₅ | " | " |
| " | " | C₃H₇ | " | " |
| " | " | —CH₂—C≡CH | " | " |
| " | " | —CH₂—CH=CH₂ | " | " |
| " | C₃H₇ | CH₃ | " | " |
| " | " | C₂H₅ | " | " |
| " | —CH₂—CH=CH₂ | CH₃ | " | " |
| " | " | C₂H₅ | " | " |
| (CH₃)₃C— | CH₃ | CH₃NH—CO— | CH₃ | " |
| " | " | " | C₂H₅ | " |
| " | " | " | —CH₂—C≡CH | " |
| " | " | " | —CH₂—CH=CH₂ | " |
| " | C₂H₅ | " | CH₃ | " |
| " | " | " | C₂H₅ | " |
| " | " | " | —CH₂—C≡CH | " |
| " | " | " | —CH₂—CH=CH₂ | " |
| " | C₃H₇ | " | CH₃ | " |
| " | " | " | C₂H₅ | " |
| " | " | " | —CH₂—C≡CH | " |
| " | " | " | —CH₂—CH=CH₂ | " |
| " | —CH₂—CH=CH₂ | " | CH₃ | " |
| " | " | " | C₂H₅ | " |
| R¹ + R² $\begin{array}{c} CH_3 \\ \| \\ -C-CH_2- \\ \| \\ CH_3 \end{array}$ | | " | CH₃ | " |
| " | | " | C₂H₅ | " |
| " | | " | —CH₂—C≡CH | " |
| " | | " | —CH₂—CH=CH₂ | " |
| —CH₂—CH₂— | | CH₃NH—CO | CH₃ | " |
| " | | " | C₂H₅ | " |
| " | | " | —CH₂—C≡CH | " |
| " | | " | —CH₂—CH=CH₂ | " |
| R¹ + R² —CH₂—CH₂—CH₂— | | " | CH₃ | " |
| " | | " | C₂H₅ | " |
| " | | " | —CH₂—C≡CH | " |
| " | | " | —CH₂—CH=CH₂ | " |
| (CH₃)₂HC— | CH₃ | CH₃NH—CO— | CH₃ | " |
| " | " | " | C₂H₅ | " |
| " | " | " | —CH₂—C≡CH | " |
| " | " | " | —CH₂—CH=CH₂ | " |
| " | C₂H₅ | " | CH₃ | " |
| " | " | " | C₂H₅ | " |
| " | " | " | —CH₂—C≡CH | " |
| " | " | " | —CH₂—CH=CH₂ | " |
| " | C₃H₇ | " | CH₃ | " |
| " | " | " | C₂H₅ | " |
| " | " | " | —CH₂—C≡CH | " |
| " | " | " | —CH₂—CH=CH₂ | " |
| " | —CH₂—CH=CH₂ | " | CH₃ | " |
| " | " | " | C₂H₅ | " |
| $\begin{array}{c} CH_3 \\ \| \\ CH_3S-C- \\ \| \\ CH_3 \end{array}$ | CH₃ | " | CH₃ | " |

-continued $$R^1-C=N-O-R^4 \atop R^2X-C=N-O-R^3 \quad (I)$$

| R¹ | R² | R³ | R⁴ | X |
|---|---|---|---|---|
| " | " | " | C₂H₅ | " |
| " | " | " | —CH₂—C≡CH | " |
| " | " | " | —CH₂—CH=CH₂ | " |
| " | C₂H₅ | " | CH₃ | " |
| " | " | " | C₂H₅ | " |
| " | " | " | —CH₂—C≡CH | " |
| " | " | " | —CH₂—CH=CH₂ | " |
| " | C₃H₇ | " | CH₃ | " |
| " | " | " | C₂H₅ | " |
| " | —CH₂—CH=CH₂ | " | CH₃ | " |
| " | " | " | C₂H₅ | " |
| FCH₂—C(CH₃)₂— | CH₃ | " | CH₃ | " |
| " | " | " | C₂H₅ | " |
| " | " | " | —CH₂—C≡CH | " |
| " | " | " | —CH₂—CH=CH₂ | " |
| " | C₂H₅ | " | CH₃ | " |
| " | " | " | C₂H₅ | " |
| " | " | " | —CH₂—C≡CH | " |
| " | " | " | —CH₂—CH=CH₂ | " |
| " | C₃H₇ | " | CH₃ | " |
| " | " | " | C₂H₅ | " |
| " | —CH₂—CH=CH₂ | " | CH₃ | " |
| " | " | " | C₂H₅ | " |
| ClCH₂—C(CH₃)₂— | CH₃ | " | CH₃ | " |
| " | " | " | C₂H₅ | " |
| " | " | " | —CH₂—C≡CH | " |
| " | " | " | —CH₂—CH=CH₂ | " |
| " | C₂H₅ | " | CH₃ | " |
| " | " | " | C₂H₅ | " |
| " | " | " | —CH₂—C≡CH | " |
| " | " | " | —CH₂—CH=CH₂ | " |
| " | C₃H₇ | " | CH₃ | " |
| " | " | " | C₂H₅ | " |
| " | —CH₂—CH=CH₂ | " | CH₃ | " |
| " | " | " | C₂H₅ | " |
| FCH₂—C(CH₂F)(CH₃)— | CH₃ | " | CH₃ | " |
| " | " | " | C₂H₅ | " |
| " | " | " | —CH₂—C≡CH | " |
| " | " | " | —CH₂—CH=CH₂ | " |
| " | C₂H₅ | " | CH₃ | " |
| " | " | " | C₂H₅ | " |
| " | " | " | —CH₂—C≡CH | " |
| " | " | " | —CH₂—CH=CH₂ | " |
| " | C₃H₇ | " | CH₃ | " |
| " | " | " | C₂H₅ | " |
| " | —CH₂—CH=CH₂ | " | CH₃ | " |
| " | " | " | C₂H₅ | " |
| CH₃ | CH₃ | " | CH₃ | " |
| " | " | " | C₂H₅ | " |
| " | " | " | —CH₂—C≡CH | " |
| " | " | " | —CH₂—CH=CH₂ | " |
| " | C₂H₅ | " | CH₃ | " |
| " | " | " | C₂H₅ | " |
| " | " | " | —CH₂—C≡CH | " |
| " | " | " | —CH₂—CH=CH₂ | " |
| " | C₃H₇ | " | CH₃ | " |
| " | " | " | C₂H₅ | " |
| " | " | " | —CH₂—C≡CH | " |
| " | " | " | —CH₂—CH=CH₂ | " |

$$R^1-C=N-O-R^4 \atop R^2X-C=N-O-R^3 \qquad (I)$$

| $R^1$ | $R^2$ | $R^3$ | $R^4$ | X |
|---|---|---|---|---|
| " | —CH₂—CH=CH₂ | " | CH₃ | " |
| " | " | " | C₂H₅ | " |

The hydroxamic acid esters of the formula (I) are prepared by reacting the oximes of the formula (II) with isocyanates of the formula (III).

If 1-methoximino-1-methylmercapto-2-hydroximino-3,3-dimethyl-butane and methyl isocyanate are used as starting substances, the course of the reaction can be represented by the following equation:

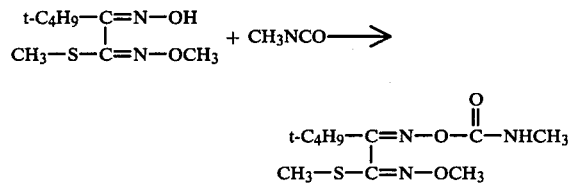

If 2-methoximino-1-methylmercapto-1-hydroximino-propane and methyl isocyanate are used as starting substances, the course of the reaction can be represented by the following equation:

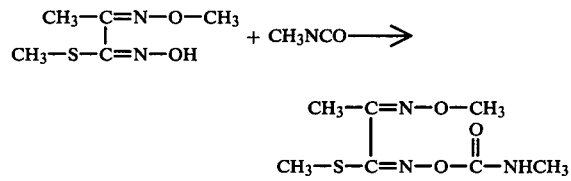

The compounds of the formula (I) are prepared by reacting the oximes of the formula (II) with isocyanates of the formula (III), if appropriate in an inert organic diluent and with the addition of a catalyst (such as triethylamine or an organic tin compound, e.g. dibutyltin dilaurate).

Diluents which may be mentioned are hydrocarbons (such as benzene, toluene, cyclohexane or petroleum ether), halogenated hydrocarbons (such as chloroform, methylene chloride or chlorobenzene), ethers (such as diethyl ether, dioxane or tetrahydrofuran), ketones (such as acetone or methyl isobutyl ketone) and ethyl acetate.

In general a molar ratio of oximes of the formula (II) to isocyanates of the formula (III) of 1:1 is used for the preparation. An excess of the isocyanates of the formula (III) can also preferably be used.

The reaction is generally carried out at temperatures from 0° to 100° C. and under a pressure of 1 bar.

The oximes of the formula (II) are novel. Preferred oximes of the formula (II) are those in which the radicals $R^1$, $R^2$ and X have the meanings given in the definitions of the preferred and particularly preferred compounds of the formula (I), and one of the radicals $R^6$ or $R^7$ represents a hydrogen atom and the other radical $R^6$ or $R^7$ represents a $C_{1-4}$alkyl, $C_{2-4}$alkenyl or $C_{2-4}$alkinyl radical, or $C_{1-4}$halogenoalkyl with up to 3 halogen atoms, or alkoxyalkyl radical with up to 2 carbon atoms in each alkyl part, and, especially, represents a methyl, ethyl, propargyl or allyl radical.

Some of the oximes of the formula (II) are obtained by reacting ketones of the formula (IV), in the case where $R^8$ represents hydrogen, with hydroxylamine ethers, or salts thereof, of the formula (V) generally in the presence of an organic solvent (such as ethanol) and if appropriate in the presence of an auxiliary base (such as sodium acetate) generally at a temperature between 20° C. and 120° C., preferably between 50° and 100° C. The compounds of formula (II) are isolated in the customary manner, for example by adding water to the reaction mixture and filtering off the precipitate. If necessary, the oximes can also be purified by recrystallization.

Some of the oximes of the formula (II) are obtained by reacting the ketones of the formula (IV), in the case where $R^8$ has the meaning given in the definition of $R^7$, with hydroxylamine, or its salts, generally in the presence of an organic solvent (such as ethanol), and if appropriate in the presence of an auxiliary base (such as sodium acetate) generally at a temperature between 20° C. and 120° C., preferably between 50° and 100° C. The compounds (II) are isolated in the customary manner, for example by adding water to the reaction mixture and filtering off the precipitate. If necessary, the oximes can also be purified by recrystallization.

Some of the ketones of the formula (IV) are new ($R^8$=H, see DOS (German Published Specification) No. 2,111,459). Preferred ketones of the formula (IV) are those of the radicals $R^1$, $R^2$, $R^8$ and X have the meanings given in the case of the preferred and particularly preferred oximes of the formula (II) or in the case of the preferred and particularly preferred hydroxamic acid esters of the formula (I). They are obtained, in the case where $R^8$ represents hydrogen, by treating ketones of the formula (VI) with nitrosating agents generally in the presence of a base (such as sodium methylate) and generally in the presence of a diluent (such as ethanol or methanol).

After acidification of the mixture the keto derivatives of the formula (V) can be isolated in the customary manner.

Examples of suitable nitrosating agents which may be mentioned for reaction variant (α) for the production of ketones of formula (IV) are: nitrosyl chloride, methyl nitrite, ethyl nitrite, propyl nitrite and isoamyl nitrite.

The ketones and nitrosating agents are generally employed in a molar ratio of 1:1.

The reaction is carried out at a temperature from 0° to 100° C. and under a pressure from 1 to 2 bars.

The novel ketones of the formula (IV) in which $R^8$ represents the radicals given in the definition of $R^7$ are obtained by reacting α-keto-oximes of the formula (VII) with compounds of the formula (VIII).

The α-keto-oximes of the formula (VII) are preferably employed in the form of their alkali metal salts. These alkali metal salts can be produced, for example, with the aid of a base (such as sodium hydride) in an inert solvent (such as dimethylformamide) or with the aid of an alkali metal carbonate (such as potassium carbonate) in a solvent (such as acetone). A preferred embodiment consists in reacting the ketones of the formula (VII) with compounds of the formula (VIII) in a two-phase system (such as aqueous sodium hydroxide solution or potassium hydroxide solution/toluene or methylene chloride) with the addition of 0.1 to 1 mole of a phase transfer catalyst (such as an ammonium or phosphonium compound, triethylbenzylammonium chloride being mentioned as an example).

In general, the reaction is carried out at a temperature between 20° and 100° C., preferably between 20° and 80° C.

Compounds of the formula (VIII) are known alkylating agents. Preferred examples which may be mentioned are: dimethyl sulfate, diethyl sulfate, allyl chloride, allyl bromide, propargyl chloride, propargyl bromide and methallyl chloride.

Ketones of the formula (VI) are known (see DOS (German Published Specification) No. 2,216,838 and German Pat. No. 2,033,454).

They are obtained by methods analogous to known methods, for example by reacting a compound of the general formula

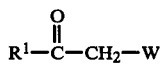  (IX)

in which $R^1$ and W have the abovementioned meaning, with a compound of the general formula

  (X)

in which
$R^2$ has the abovementioned meaning and
X represents O or S.

The active compounds are well tolerated by plants, have a favorable level of toxicity to warm-blooded animals, and are suitable for combating arthropod pests, especially insects and arachnida, and nematodes, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example *Reticulitermes* spp.;

from the order of the Anoplura, for example *Phylloxera vastatrix, Pemphigus* spp., *Pediculus humanus corporis, Haematopinus* spp. and *Linognathus* spp.;

from the order of the Mallophaga, for example *Trichodectes* spp. and *Damalinea* spp.;

from the order of the Thysanoptera, for example *Hercinothrips femoralis* and *Thrips tabaci;* from the order of the Heteroptera, for example *Eurygaster* spp., *Dysdercus intermedius, Piesma quadrata, Cimex lectularius, Rhodnius prolixus* and *Triatoma* spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica;* from the order of the Hymenoptera, for example *Diprion* spp., *Hoplocampa* spp., *Lasius* spp., *Monomorium pharaonis* and *Vespa* spp.;

from the order of the Diptera, for example *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa;* from the order of the Siphonaptera, for example *Xenopsylla cheopis* and *Ceratophyllus* spp.;

from the class of the Arachnida, for example *Scorpio maurus* and *Latrodectus mactans;* from the order of the Acarina, for example *Acarus siro, Argas* spp., *Ornithodoros* spp., *Dermanyssus gallinae, Eriophyes ribis, Phyllocop ruta oleivora, Boophilus* spp.,

*Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp.

The plant-parasitic nematodes include *Pratylenchus* spp., *Radopholus similis, Ditylenchus dipsaci, Tylenchulus semipenetrans, Heterodera* spp., *Meloidogyne* spp., *Aphelenchoides* spp., *Longidorus* spp., *Xiphinema* spp., and *Trichodorus* spp.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in their commercially available formulations and in the use forms, prepared from these formulations, as a mixture with other active compounds, such as insecticides, baits, sterilising agents, acaricides, nematicides, fungicides, growth-regulating substances or herbicides. The insecticides include, for example, phosphates, carbamates, carboxylates, chlorinated hydrocarbons, phenylureas and, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against pests harmful to health and pests of stored products, the active compounds are distinguished by an excellent residual action on wood and clay as well as a good stability to alkali on limed substrates.

The active compounds according to the invention are also suitable for combating ectoparasites and endoparasites in the field of veterinary medicine.

The present invention also provides a pesticidal composition containing as active ingredient a compound of the present invention in admixture with a solid or liquefied gaseous diluent or carrier or in admixture with a liquid diluent or carrier containing a surface-active agent.

The present invention also provides a method of combating pests (in particular arthropods, especially insects or acarids, and nematodes) which comprises applying to the pests, or to a habitat thereof, a compound of the present invention alone or in the form of a composition containing as active ingredient a compound of the present invention in admixture with a diluent or carrier.

The present invention also provides a method of freeing or protecting domesticated animals from parasites which comprises applying to said animals a compound according to the present invention, in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasites by the application to said animals of a compound according to the present invention, in admixture with a diluent or carrier.

The active compounds according to the invention may be used in a known manner in the veterinary sector, such as by oral administration, for example in the form of tablets, capsules, drinks and granules, by dermal application, for example by means of dipping, spraying, pouring on and spotting on, and dusting, and by parenteral administration, for example by means of an injection.

PREPARATIVE EXAMPLES

Example 1

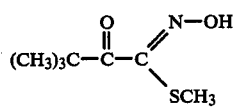 (a)

146 g (1 mole) of 1-methyl-mercaptopinacolin were mixed with 180 g of 30% strength sodium methylate solution in methanol, and 117.2 g of iso-amyl nitrite were added dropwise at 0° C., while cooling. The batch was then allowed to come slowly to room temperature.

The mixture was stirred at room temperature for a further 4 hours, most of the methanol was removed in vacuo, water was added to the residue, the aqueous solution was extracted 3 times by shaking with chloroform, the aqueous phase was neutralized with concentrated hydrochloric acid and the product was extracted by shaking with methylene chloride. After drying the organic phase over sodium sulphate, the solvent was removed in vacuo and the residue was crystallized with petroleum ether.

Yield: 116 g (66% of theory).
Melting Point: 59° to 62° C.

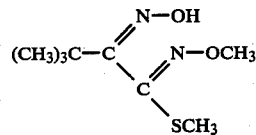 (b)

73.8 g (0.39 mole) of 3,3-dimethyl-1-methoximino-1-methylmercapto-butan-2-one, 81.3 g (1.17 mole) of hydroxylamine hydrochloride and 95.9 g (1.17 moles) of sodium acetate were dissolved in 500 ml of ethanol and the solution was boiled under reflux for 4 hours. After adding the same amount of hydroxylamine hydrochloride and sodium acetate, the reaction mixture was boiled under reflux for a further 4 hours and then largely freed from the solvent in vacuo. Water was added to the residue, the acetic acid formed was neutralized with sodium bicarbonate solution and the product was extracted with methylene chloride. After drying the organic phase over sodium sulphate, the solvent was stripped off in vacuo and, after triturating the residue with diisopropyl ether, the product was filtered off.

Yield: 57.1 g (72% of theory).
Melting Point: 137° to 138° C.

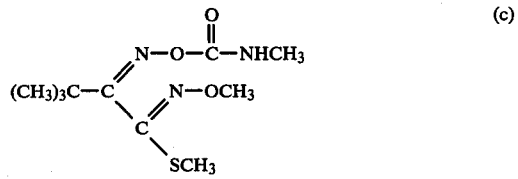 (c)

37.6 g (0.66 mole) of methyl isocyanate were added dropwise to 68.8 g (0.33 mole) of 3,3-dimethyl-2-hydroximino-1-methoximino-1-methylmercapto-butane in 250 ml of methylene chloride, while stirring. The mixture was then boiled under reflux for a further hour and the solvent and excess methyl isocyanate were removed in vacuo. The crystalline residue was stirred with petroleum ether and filtered off.

Yield: 85.1 g (99% of theory).
Melting Point: 155°–156° C.

Example 2

 (a)

A mixture of 45 g (0.33 mole) of 1-methylthio-1-oximino-propan-2-one, 56 g (0.67 mole) of hydroxylamine methyl ether hydrochloride, 55 g (0.67 mole) of sodium acetate and 400 ml of ethanol was heated under reflux for 2 hours.

The reaction mixture was concentrated to half the volume and taken up in dilute KOH. The mixture was extracted twice with CHCl$_3$ and the aqueous solution was adjusted to pH 5 to 6 with HCl. The H$_2$O phase was then extracted three times with CHCl$_3$, dried over Na$_2$SO$_4$ and concentrated. Distillation in a bulb tube oven at 150° to 170° C./0.3 mm Hg gave about 40 g of a water-clear viscous oil, which gradually crystallized out.

Yield: 70% of theory of 1-methylthio-1-oximino-2-methoximino-propane.
Melting Point: 52° to 74° C.

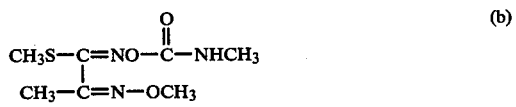 (b)

Several drops of triethylamine were added to a mixture of 2.0 g (0.0123 mole) of 1-methylthio-1-oximino-2-methoximino-propane and an excess of 2 g of methyl isocyanate in 30 ml of absolute acetone. After stirring the mixture at room temperature for 5 hours, the solvent was distilled off. The residue was taken up in chloroform and the organic phase was extracted twice by shaking with H$_2$O, dried over Na$_2$SO$_4$ and concentrated.

Yield: 2.3 g (86% of theory).
$n_D^{20}$: 1.5330.

The following compounds were prepared analogously to Examples 1 and 2:

$$R^1-C=N-OR^4$$
$$R^2X-C=N-OR^3$$

| Compound No. | $R^1$ | $R^2$ | $R^3$ | $R^4$ | X | Melting point: |
|---|---|---|---|---|---|---|
| 3 | $(CH_3)_3C$ | $CH_3$ | $C_2H_5$ | $-\overset{O}{\underset{\parallel}{C}}-NHCH_3$ | S | 92–94° C. |
| 4 | $(CH_3)_3C$ | $CH_3$ | $-CH_2-CH=CH_2$ | $-\overset{O}{\underset{\parallel}{C}}-NHCH_3$ | S | Viscous oil |
| 5 | $CH_3$ | $CH_3$ | $-\overset{O}{\underset{\parallel}{C}}-NHCH_3$ | $C_2H_5$ | S | $n_D^{20}$: 1.5232 |
| 6 | $CH_3$ | $C_2H_5$ | $-\overset{O}{\underset{\parallel}{C}}-NHCH_3$ | $CH_3$ | S | $n_D^{20}$: 1.5165 |
| 7 | $CH_3$ | $C_2H_5$ | $-\overset{O}{\underset{\parallel}{C}}-NHCH_3$ | $C_2H_5$ | S | $n_D^{20}$: 1.5114 |
| 8 | $CH_3$ | $CH_3$ | $CH_3$ | $-\overset{O}{\underset{\parallel}{C}}-NHCH_3$ | S | $n_D^{20}$: 1.5280 |
| 9 | $CH_3$ | $CH_3$ | $C_2H_5$ | $-\overset{O}{\underset{\parallel}{C}}-NHCH_3$ | S | $n_D^{20}$: 1.5207 |
| 10 | $-(CH_2)_3-$ | | $-\overset{O}{\underset{\parallel}{C}}-\overset{H}{\underset{\mid}{N}}-CH_3$ | $CH_3$ | S | $n_D^{20}$: 1.5478 |
| 11 | $(CH_3)_3C$ | $CH_3$ | $-\overset{O}{\underset{\parallel}{C}}-\overset{H}{\underset{\mid}{N}}-CH_3$ | $CH_3$ | S | viscous oil |

The pesticidal activity of compounds of this invention is illustrated by the following examples wherein the compounds according to the present invention are each identified by the number (given in brackets) from the examples and table hereinabove.

Example 3

Phaedon Larvae Test

Solvent: 3 parts by weight of dimethylformamide
Emulsifier: 1 part by weight of alkylaryl polyglycol ether To produce a suitable preparation of active compound, 1 part by weifht of active compound was mixed with the stated amount of solvent and the stated amount of emulsifier, and the concentrate was diluted with water to the desired concentration.

Cabbage leaves (*Brassica oleracea*) were treated by being dipped into the preparation of the active compound of the desired concentration and were infested with mustard beetle larvae (*Phaedon cochleariae*), as long as the leaves were still wet.

After the specified periods of time, the destruction in % was determined. 100% meant that all the beetle larvae had been killed; 0% meant that none of the beetle larvae had been killed.

In this test, for example, the following compounds showed a superior activity compared to the prior art: (1), (2), (3), (6) and (9).

Example 4

Laphygma Test

Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Cabbage leaves (*Brassica oleracea*) were treated by being dipped into the preparation of active compound of the desired concentration and were infested with caterpillars of the owlet moth (*Laphygma frugiperda*), as long as the leaves were still moist.

After the specified periods of time, the destruction in % was determined. 100% meant that all the caterpillars had been killed; 0% meant that none of the caterpillars had been killed.

In this test, for example, the following compounds showed a superior activity compared to the prior art: (1), (2), (3) and (6).

Example 5

Tetranychus Test (resistant)

Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Bean plants (*Phaseolus vulgaris*) which were heavily infested with the common spider mite or two-spotted spider mite (*Tetranychus urticae*) in all stages of development were treated by being dipped into the preparation of the active compound of the desired concentration.

After the specified periods of time, the destruction in % was determined. 100% meant that all the spider mites had been killed; 0% meant that none of the spider mites had been killed.

In this test, for example, the following compound showed a superior activity compared to the prior art: (6).

Example 6

Critical Concentration Test/Soil Insects

Test insect: *Phorbia antiqua* (in the soil)
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l) being decisive. The soil was filled into pots and the pots were left to stand at room temperature.

After 24 hours, the test animals were introduced into the treated soil, and after a further 2 to 7 days the degree of effectiveness of the active compound was determined in % by counting the dead and live test insects. The degree of effectiveness was 100% if all the test insects had been killed and was 0% if just as many test insects were still alive as in the case of the untreated control.

In this test, for example, the following compounds showed a superior action compared to the prior art: (2) and (3).

It will be appreciated that the instant specification and examples are set forth by way of illustration and not limitation, and that various modifications and changes may be made without departing from the spirit and scope of the present invention.

We claim:

1. A hydroxamic acid ester of the formula

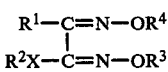

in which
  $R^1$ is an alkyl radical with 1 to 4 carbon atoms, a halogenoalkyl radical with 1 to 4 carbon atoms and up to 5 halogen atoms, a cycloalkyl radical with up to 8 carbon atoms, an alkoxyalkyl or alkylthioalkyl radical with up to 3 carbon atoms in each alkyl part, or an optionally substituted phenyl radical,
  $R^2$ is an alkyl radical with 1 to 4 carbon atoms, an alkenyl radical with 1 to 4 carbon atoms or an alkinyl radical with 1 to 4 carbon atoms, or
  $R^1$ and $R^2$ together are an optionally methyl-substituted methylene, ethylene or propylene bridge,
  one of the radicals $R^3$ and $R^4$ is an alkyl radical with 1 to 4 carbon atoms, an alkenyl radical with 2 to 4 carbon atoms, a halogenoalkyl radical with 1 to 4 carbon atoms and up to 3 halogen atoms, a halogenoalkenyl radical with 2 to 4 carbon atoms and up to 3 halogen atoms or an alkoxyalkyl radical with up to 2 carbon atoms in each alkyl part, while the other of $R^3$ or $R^4$ is

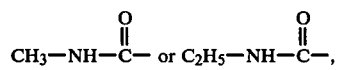

and X is O or S.

2. A compound according to claim 1, in which X is S.

3. A compound according to claim 1, in which
  $R^1$ is a methyl, ethyl, propyl, isopropyl, tert.-butyl or fluoro-, chloro-, bromo-, difluoro- or dichloro-tert.-butyl radical, and
  $R^2$ is a methyl or ethyl radical, or
  $R^1$ and $R^2$ together are an ethylene bridge, and one of the radicals $R^3$ and $R^4$ is a methyl, ethyl, propargyl or allyl radical while the other is

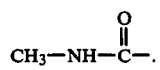

4. A compound according to claim 1, wherein such compound is 3,3-dimethyl-2-(N-methylcarbamoyloximino)-1-methoximino-1-methylmercapto-butane of the formula

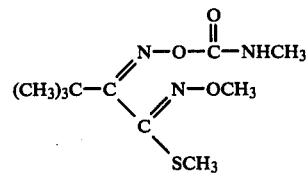

5. A compound according to claim 1, wherein such compound is 2-methoximino-1-methylmercapto-1-(N-methylcarbamoyloximino)propane of the formula

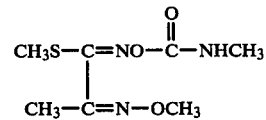

6. A compound according to claim 1, wherein such compound is 3,3-dimethyl-2-(N-methylcarbamoyloximino)-1-ethoximino-1-methylmercapto-butane of the formula

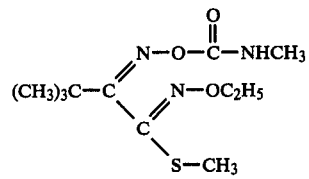

7. A compound according to claim 1, wherein such compound is 2-methoximino-1-ethylmercapto-1-(N-methylcarbamoyloximino)propane of the formula

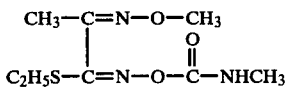

8. A compound according to claim 1, wherein such compound is 1-ethoximino-1-methylmercapto-2-(N-methylcarbamoyloximino)propane of the formula

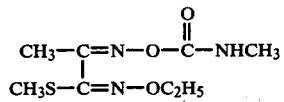

9. A pesticidal composition comprising a pesticidally effective amount of a compound according to claim 1 in admixture with a diluent.

10. A method of combating pests, comprising applying to the pests, or to a habitat thereof, a pesticidally effective amount of a compound according to claim 1.

11. A method according to claim 10, wherein such compound is
3,3-dimethyl-2-(N-methylcarbamoyloximino)-1-methoximino-1-methylmercapto-butane,
2-methoximino-1-methylmercapto-1-(N-methylcarbamoyloximino)propane,
3,3-dimethyl-2-(N-methylcarbamoyloximino)-1-ethoximino-1-methylmercapto-butane,
2-methoximino-1-ethylmercapto-1-(N-methylcarbamoyloximino)propane or
1-ethoximino-1-methylmercapto-2-(N-methylcarbamoyloximino)propane.

* * * * *